United States Patent [19]

Deppert et al.

[11] Patent Number: 5,254,335
[45] Date of Patent: Oct. 19, 1993

[54] HAIR CONDITIONING COMPOUNDS CONTAINING REACTIVE NONIONIC SURFACTANTS AND ISOTHIURONIUM COMPOUNDS AND METHOD OF USE

[75] Inventors: Thomas M. Deppert, Waterbury; Janusz Z. Jachowicz, Bethel, both of Conn.

[73] Assignee: Clairol Incorporated, New York, N.Y.

[21] Appl. No.: 918,886

[22] Filed: Jul. 23, 1992

Related U.S. Application Data

[62] Division of Ser. No. 595,073, Oct. 10, 1990, abandoned.

[51] Int. Cl.[5] .................. A61K 7/06; C07C 335/32; C07F 7/04; C07F 7/10
[52] U.S. Cl. ........................... 424/70; 424/71; 556/424; 556/425; 558/4; 558/5
[58] Field of Search .................. 558/4, 5; 424/70, 71; 556/424, 425

[56] References Cited

U.S. PATENT DOCUMENTS

| | | | |
|---|---|---|---|
| 2,146,744 | 2/1939 | Johnson | 558/4 |
| 2,270,893 | 1/1940 | Orthner et al. | 558/5 |
| 2,275,379 | 3/1942 | Johnson | 558/5 X |
| 2,331,387 | 10/1943 | Graenacher et al. | 558/5 X |
| 2,510,739 | 6/1950 | Clemence et al. | 558/4 |
| 2,514,650 | 7/1950 | Knott et al. | 558/5 X |
| 2,547,366 | 4/1951 | Bock et al. | 558/5 |
| 2,607,803 | 8/1952 | Lecher et al. | 558/5 |
| 2,624,762 | 11/1952 | Downey | 558/5 |
| 2,640,079 | 5/1953 | Benneville et al. | 558/4 |
| 2,792,414 | 5/1957 | Walton | 558/5 |
| 2,906,773 | 9/1959 | Trapp | 558/4 |
| 3,222,396 | 12/1965 | Williams | 558/5 X |
| 3,371,010 | 2/1968 | Hamilton et al. | 558/4 X |

Primary Examiner—Floyd D. Higel
Attorney, Agent, or Firm—Wyatt, Gerber, Burke and Badie

[57] ABSTRACT

Novel isothiuronium surfactant salts are useful as hair conditioning agents. Aqueous composition containing such salts, and method of using the salts are disclosed.

24 Claims, No Drawings

HAIR CONDITIONING COMPOUNDS CONTAINING REACTIVE NONIONIC SURFACTANTS AND ISOTHIURONIUM COMPOUNDS AND METHOD OF USE

This application is a division application of co-pending application Ser. No. 07/595,073, filed Oct. 10, 1990, now abandoned.

BACKGROUND OF THE INVENTION

1. FIELD OF THE INVENTION

This invention is in the field of human hair conditioners to make such hair more manageable.

The invention, which utilizes novel compounds, relates to a process for conditioning human hair especially, although not necessarily after waving. It relates also to compositions containing the novel compounds. More particularly, it relates to certain water soluble isothiuronium salts and to the utility of such salts as hair conditioners.

2. RELATED ART

A technique of hair treatment involving the introduction of nonpolar residues into the hair structure has been reported by Hall and Wolfram, J. Soc. Cosmet. Chem., 28 231 (1977). This work was based on an earlier report that the wet mechanical properties of reduced keratin fibers could be restored without crosslinking by incorporating high molecular weight alkyl-monohalides into the fiber structure. (See British Patent 2,197,887). Successful mechanical recovery of alkylated fibers was attributed to the hydrophobic interactions between alkyl moieties. Qualitatively similar effects can be achieved by introducing other alkyl hydrophobic groups into keratin as reported in U.S. Pat. No. 2,548,679. These effects were achieved by assuming a reduction in the water content and thus increased viscosity of the keratin protein. These compounds are, however, partially to completely insoluble in water. The reagents were suspended in aqueous media or dissolved in organic solvents to be utilized in treating hair keratin.

None of these procedures have been completely satisfactory and much effort has been expended seeking improved hair conditioners, especially durable hair conditioners which will remain effectively in human hair despite repeated washings.

SUMMARY OF THE INVENTION

It has now been discovered that certain novel water soluble compounds containing at least one isothiuronium salt will bind to keratin protein, and impart a conditioning effect to human hair. They are salts suitably halides, preferably a bromide or iodide. These compounds can be employed as hair conditioners which will continue to provide their beneficial conditioning effects through several shampoos. This invention is concerned with such compounds, hair conditioning compositions containing one or more of these compounds and methods of employing them to improve the combability of hair.

DETAILED DESCRIPTION

The novel compounds useful in this invention are water soluble surfactants useful as conditioners for human hair. They may be represented by the formulas:

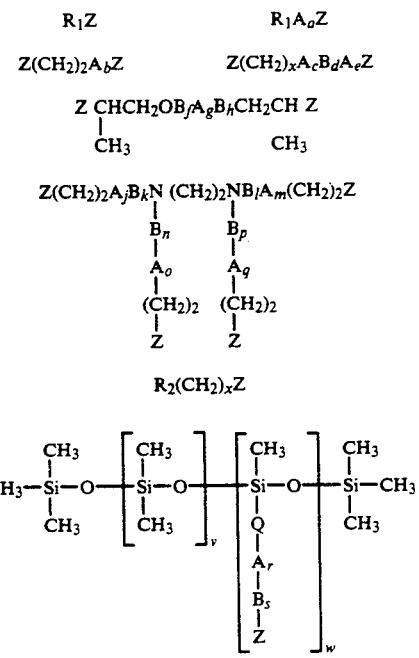

wherein:
$R_1$ is an alkyl or arylalkyl, the alkyl having about 12 to 24 carbons;
$R_2$ is a perfluoroalkyl having about 4 to 16 carbons;
A is an ethoxy group;
B is a propoxy group;
Z is an isothiuronium halide group;
Q is an alkylene group having about 2 to 5 carbon atoms;
a through s are integers designating, as the case may be, the degree of ethoxylation and/or propoxylation, v is an integer of about 5 to 500, w is an integer of about 5 to 200 and x is an integer from about 0 to 4.

The compounds of the invention can be prepared by any of a number of procedures known to those skilled in the art.

For example, the salts can be prepared by reaction of the corresponding bromides and thiourea in a reaction inert, polar, organic solvent such as ethanol at a temperature of from about 50° to about 80° C. for from about 4 to about 6 hours. If a precipitate forms upon cooling, it is filtered and recrystallized from ethanol. If no precipitate forms upon cooling, then the ethanol is removed by rotary evaporation and the residue is employed without further purification. The methods for the preparation of the monobromides and the necessary starting compounds are known. The dibromides can be prepared from the corresponding dialcohols by reaction with a molar excess of phosphorous tribromide in an organic hydrocarbon solvent such as benzene.

Compounds A through K, the formulas of which are shown hereinafter and mixtures of these compounds have been prepared using these general procedures.

Compound A was isolated as a mixture containing an alcohol soluble fraction and an alcohol insoluble fraction.

The hair conditioning agents of this invention have a number of advantages compared to hair conditioners of the prior art. Their principal advantage is that they are very durable and will remain in the hair as effective conditioners even after several shampoos, e.g. four to eight or more. Their durability is attributable to at least two factors. One is that they form ionic bonds with the hair. The other is that they form covalent bonds with the hair. Additionally, under certain conditions they may be insolubilized on or near the surface of the hair and provide a conditioning effect.

As is known, the keratin of human hair carries an anionic charge. The hair conditioners of the invention are electrostatically attracted and bound to the hair. Human hair, especially after waving with reducing agents such as thioglycolic acid has a number of free mercaptan groups formed by reductive cleavage of the disulfide bonds of cystine. The compounds of this invention may react with the free mecrcaptan groups to form covalent bonds which bind the conditioner to the hair. The presence of the long chain moiety shown in the above general formulas chemically joined with the hair improves the lubricity. As a result of these reactions, the combability of the hair is greatly improved.

The reaction for the formation of covalent bonds for certain of the compounds of the invention is illustrated below wherein R represents the balance of the molecule and K represents keratin protein.

Reduction

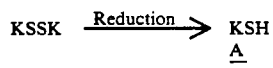

For Monoisothiuronium Compounds at Low pH

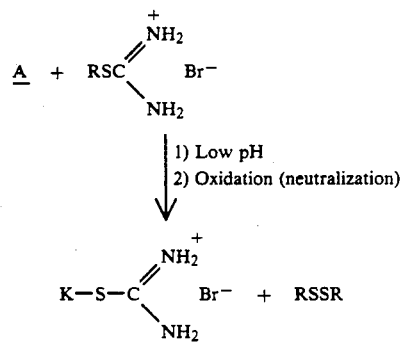

For Monoisothiuronium Salts At High pH

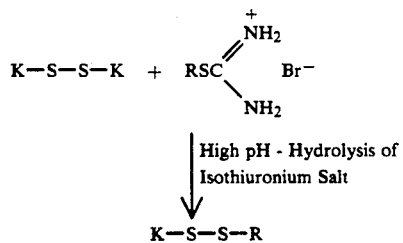

The isothiuronium salts can be incorporated into waving lotions and interact with hair by oxidation during the neutralization process. These salts can also react with untreated hair in an aqueous medium at high pH by thiol/disulfide exchange reactions.

Dyed hair (which becomes alkaline during the dyeing process), exposed to a solution of unhydrolyzed perfluoralkyl isothiuronium salts causes hydrolysis and precipitation of the surfactant. This layer may be durable to shampooing as shown by the combing data hereinbelow, and the cause of the dramatic increase in the hydrophobicity of dyed as well as bleached and waved (reduced) hair.

The results shown herein suggest that, under specific conditions, there is a chemical reaction of isothiuronium compounds with keratin. However, we do not wish to be bound by any theory and the contribution of electrostatic or hydrophobic interactions cannot be excluded, especially in view of the fact that the surfactants containing short polyoxyalkylene chains are characterized by much lower solubility after hydrolysis.

It should be noted that the hydrolyzed isothiuronium compounds are effective in increasing the viscosity of the conditioning solutions. The maximum viscosity was observed to be dependent upon concentration, pH and the structure of the isothiuronium salt. This property increases the ease of formulation by decreasing the need for thickening agents.

The products of this invention are especially useful after waving with ammonium thioglycolate or with an inorganic reducing agent such as sodium bisulfite. However, they may also be employed with untreated or virgin hair, dyed hair, relaxed hair and bleached hair. In all cases they reduce the combing work as determined by the method of Garcia and Diaz described in J. soc. Cosmet. Chem. 27, 379-398 (September 1976).

Combability can be defined as the subjective perception of the relative ease or difficulty with which human hair can be combed. It depends on the magnitude of the forces that oppose combing.

As discussed at page 379 by Garcia and Diaz in the cited publication, which is incorporated herein by reference:

Combability is an important attribute, which is always considered when judging the "condition" of human hair. Improved combability is perceived as the hair being in better condition. Another concept closely associated with combability is that of manageability. Still another factor related to combability is that of the mechanical damage, which is done to hair with the combing process, which is accelerated if the hair is hard to comb or to untangle. It follows that combability, due to its close connection with other desirable hair qualities, is a very important factor in judging the performance of many hair care products.

The hair conditioners of this invention will normally be contacted with the hair to be treated in the form of a waving lotion or from water or water/alcohol solutions containing from about 0.1% to about 10% by weight, based on the total weight of the composition, of at least one of the conditioners. Preferred solutions will contain from about 0.5% to 5% of at least one conditioner. Aqueous solutions are preferred, but the compositions may contain up to about 30% by weight of a water miscible lower alkanol, preferably ethanol or isopropanol as well as benzyl alcohol to assist in solubilizing the conditioner or other components of the composition which may be present. The additional excipients include, for example coloring agents, fragrances, surfactants, buffers, preservatives, viscosity enhancers, gelling agents, silicones or other emulsifying agents, and other common adjuvants well known to those skilled in the art. The contact time is from about 5 to about 30 minutes.

The compositions may be provided as foams, gels, aerosols or other standard forms normally employed with such products. These may be produced by procedures well known to the skilled artisan A number of tests have been conducted with the conditioners of his invention to determine their efficiency as hair conditioning agents. These test were conducted on untreated, reduced and dyed hair at various pH values as described below. The results of the tests are shown in Tables I through V. The formulas of the compounds or mixtures tested are shown below:

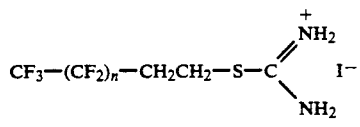

A where n = 3-13

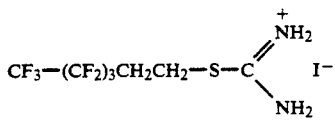

B

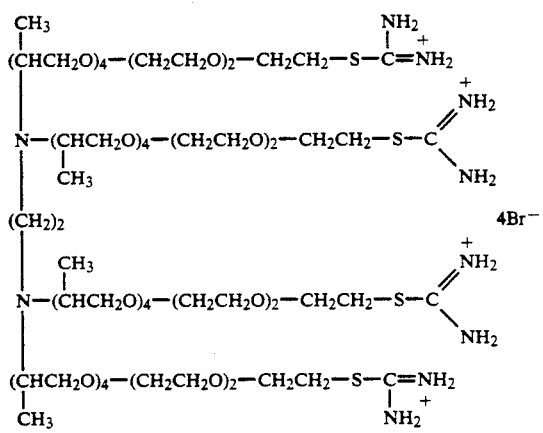

C

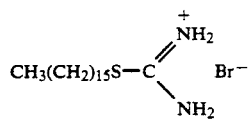

D

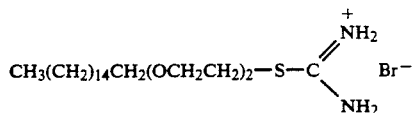

E

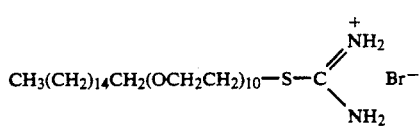

F

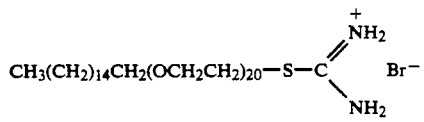

G

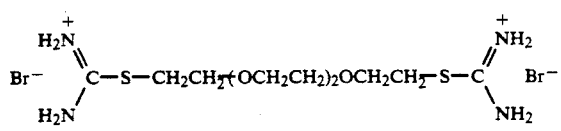

H

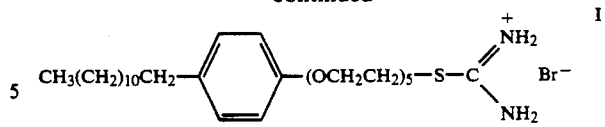

I

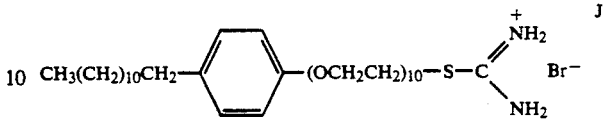

J

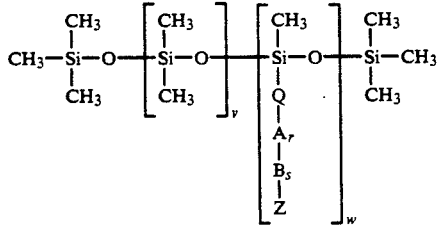

K $M_w$ - about 4200
$M_w$ - about 5200

The compounds represented as A and K are most conveniently available as mixtures and may be employed as such. This is because the starting products from which they are prepared are commercially available as mixtures. However, pure compounds can be prepared and utilized, if desired, but the effort and expense of so doing is rarely compensated by improved performance. There are two mixtures of compounds represented by Formula K that are presently conveniently available. In one such mixture, the weight average molecular weight ($M_w$) is about 4,200. In the other, it is about 5200. However, if desired, K-compounds and mixtures can be prepared for use in this invention with an $M_w$ of from about 1000 to 100,000.

In the above formula for K, the subscripts r, s, v and w have the same meaning as defined hereinabove.

WET COMBING WORK DATA

Each experiment was performed on two 6 inch, 2 g tresses of untreated brown hair. Measurements of wet combing were obtained on an Instron Model 1101 with a cross-head speed of 10 cm/min.. The results are the average of the measurements obtained for the two tresses.

In the first set of experiments, the hair tresses were treated with 25 mL of ammonium thioglycolate (6% adjusted to pH 9) for 10 min. at room temperature and rinsed with tap water for one minute. Then, the hair was exposed to 10 mL of a 1% solution (pH 6) of the conditioner being tested for 30 min. at room temperature prior to neutralization (oxidation for 8 min. with 10 mL of 3% $H_2O_2$) Subsequent shampooings entailed lathering the hair with approximately 0.5 g of Herbal Essence shampoo for 30 sec. followed by rinsing with warm tap water for 30 seconds. Table I details the results of the experiments. As can be seen from the data, the hair samples treated with the fluorosurfactant A (ethanol soluble fraction) were easily combable after 8 shampooings. The ethanol insoluble fraction of the isothiuronium fluorosurfactant A and the diamine containing four isothiuronium groups C are less effective. In addition, it was observed that compound A (ethanol soluble fraction) leaves the hair very hydrophobic through four shampooings.

The conditioning efficacy of selected surfactants as durable conditioners for dyed hair treated with the reactive surfactants at pH 6, was also tested. After dyeing with Nice 'n Easy #122 (10 g of dye solution per 2 g tress), the hair was exposed to 10 mL of a 1% solution of the corresponding conditioner for 30 min. at room temperature. The subsequent shampooing procedure is described above. The wet combing data presented in Table II indicate that the fluorosurfactants of the present invention considerably reduce the wet combing work. Isothiuronium surfactant A (ethanol insoluble fraction) was observed to significantly increase the hydrophobicity of dyed hair.

In the third set of experiments the conditioners were tested on intact (untreated) hair. The hair was exposed to 10 mL of a 1% solution of the corresponding conditioner surfactant for 30 min. at room temperature and then rinsed with warm tap water. Subsequent shampooings are as described above. Table III details the results of the experiments. As can be seen from the data, the isothiuronium surfactants produce a conditioning effect when applied to the hair from a pH 10.7 solution.

Based on results obtained in the previous studies, dyed hair was treated at pH 5.3. The results are presented in Table IV. It will be seen that the isothiuronium surfactants are useful as conditioning agents, and that compound D reduced the combing work through 8 shampooings.

Finally, several isothiuronium surfactants were applied to reduced hair from pH 5.3 solutions. The hair was treated as described above. As shown in Table V, the isothiuronium surfactants produced a conditioning effect.

TABLE I

Wet Combing Work on Reduced Hair (at pH = 6).

| Treatment | Wet Combing Work (g*cm) | | |
|---|---|---|---|
| | After Treatment | After 4 Shampoos | After 8 Shampoos |
| No Treatment | 568 | 1626 | 2096 |
| Compound H | 435 | 1259 | 1562 |
| Compound C | 336 | 738 | 1166 |
| Compound A (ethanol sol.) | 115 | 218 | 505 |
| Compound A (ethanol insol.) | 355 | 901 | 1642 |

TABLE II

Wet Combing Work on Dyed Hair (at pH = 6).

| Treatment | Wet Combing Work (g*cm) | | |
|---|---|---|---|
| | After Treatment | After 4 Shampoos | After 8 Shampoos |
| No Treatment | 1982 | 5184 | 4576 |
| Compound A (ethanol sol.) | 196 | 449 | 2142 |
| Compound A (ethanol. insol.) | 403 | 844 | 1631 |

TABLE III

Wet Combing Work on Untreated Hair (at pH = 10.7).

| Treatment | Wet Combing Work (g*cm) | | |
|---|---|---|---|
| | After Treatment | After 4 Shampoos | After 8 Shampoos |
| No Treatment | 332 | 691 | 740 |
| Compound D | 273 | 397 | 609 |
| Compound E | 248 | 379 | 560 |
| Compound F | 259 | 552 | 657 |
| Compound G | 431 | 782 | 1004 |
| Compound I | 229 | 443 | 552 |
| Compound J | 383 | 517 | 894 |

TABLE IV

Wet Combing Work on Dyed Hair (at pH = 5.3).

| Treatment | Wet Combing Work (g*cm) | | |
|---|---|---|---|
| | After Treatment | After 4 Shampoos | After 8 Shampoos |
| No Treatment | 2840 | 3128 | 4633 |
| Compound D | 407 | 683 | 1859 |
| Compound E | 334 | 1012 | 3900 |
| Compound I | 315 | 645 | 4137 |

TABLE V

Wet Combing Work on Reduced Hair (at pH = 5.3).

| Treatment | Wet Combing Work (g*cm) | | |
|---|---|---|---|
| | After Treatment | After 4 Shampoos | After 8 Shampoos |
| No Treatment | 1908 | 3670 | 5137 |
| Compound D | 626 | 536 | 630 |
| Compound E | 485 | 640 | 992 |
| Compound F | 614 | 1130 | 1734 |
| Compound G | 741 | 1350 | 1918 |
| Compound H | 391 | 640 | 660 |
| Compound I | 568 | 1027 | 945 |
| Compound K (5200) | 635 | 1872 | 2371 |
| Compound K (4200) | 378 | 1612 | 1236 |

The following non-limiting examples illustrate typical compositions within the scope of the invention.

| Prototype Conditioner Formulations Containing Reactive Fluorosurfactants: | |
|---|---|
| Ingredient | Percent |
| Formulation I. | |
| Water | 87.055 |
| Acetamide MEA | 3.000 |
| Hydrolyzed Animal Collagen | 0.700 |
| Glycol Stearate | 3.000 |
| Cetyl Alcohol | 1.300 |
| Compound A (ethanol sol. fraction) | 2.000 |
| Hydroxyethylcellulose | 0.850 |
| Polysorbate 20 | 1.000 |
| Hydrolyzed Keratin | 0.100 |
| Fragrance | 0.500 |
| Preservatives and Dyes | 0.495 |
| | 100.000 |
| Formulation II. | |
| Water | 87.055 |
| Acetamide MEA | 3.000 |
| Hydrolyzed Animal Collagen | 0.700 |
| Glycol Stearate | 3.000 |
| Cetyl Alcohol | 1.300 |
| Compound A (ethanol insol. fraction) | 2.000 |
| Hydroxyethylcellulose | 0.850 |
| Polysorbate 20 | 1.000 |
| Hydrolyzed Keratin | 0.100 |
| Fragrance | 0.500 |
| Preservatives and Dyes | 0.495 |
| | 100.000 |

These formulations are storage stable and have a viscosity and pH similar to the control formulation which contained stearalkonium chloride in place of the compounds of the invention.

TABLE VI

| | Wet Combing Work on Reduced Hair (at pH = 5.3). | | |
|---|---|---|---|
| | Wet Combing Work (g*cm) | | |
| Treatment | After Treatment | After 4 Shampoos | After 8 Shampoos |
| No Treatment | 724 | 1934 | 1924 |
| Formulation I | 344 | 673 | 1471 |
| Formulation II | 197 | 643 | 807 |

What is claimed is:

1. Aqueous compositions useful as hair conditioners for human hair containing an excipient which is acceptable in hair conditioning compositions together with a water soluble compound of the formula:

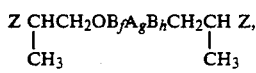

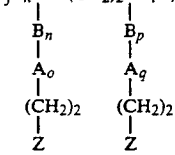

$Z(CH_2)_2A_jB_kN\!\!-\!\!(CH_2)_2NB_lA_m(CH_2)_2Z,$
with $B_n$, $A_o$, $(CH_2)_2$, $Z$ and $B_p$, $A_q$, $(CH_2)_2$, $Z$ substituents $R_2(CH_2)_xZ$ or

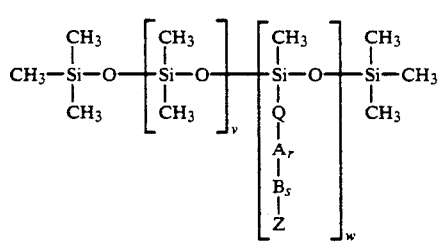

wherein:
- $R_1$ is an alkyl or arylalkyl, the alkyl having about 12 to 24 carbons;
- $R_2$ is a perfluoroalkyl having about 4 to 16 carbons;
- A is an ethoxy group;
- B is a propoxy group;
- Z is an isothiuronium halide group;
- Q is an alkylene group having about 2 to 5 carbon atoms;
- a through s are integers designating the degree of ethoxylation and/or propoxylation or both, v is an integer of about 5 to 500, w is an integer of about 5 to 200 and x is an integer from about 0 to 4 in an amount which is effective when hair is treated by contact with the composition for from about 5 to about 30 minutes to improve the combability of the hair compared with hair which has not been so treated.

2. A composition as in claim 1 wherein the water soluble compound is of the formula:

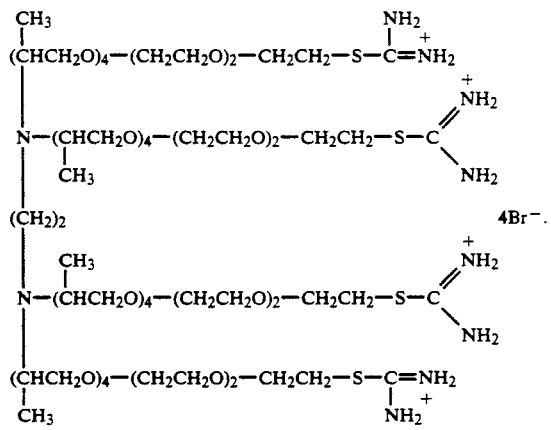

3. A composition as in claim 1 wherein the water soluble compound is of the formula:

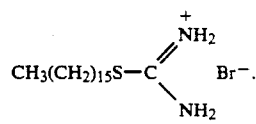

4. A composition as in claim 11 wherein the water soluble compound is of the formula:

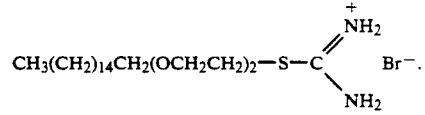

5. A composition as in claim 1 wherein the water soluble compound is of the formula:

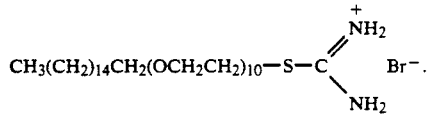

6. A composition as in claim 1 wherein the water soluble compound is of the formula:

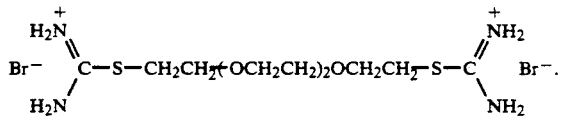

7. A composition as in claim 1 wherein the water soluble compound is of the formula:

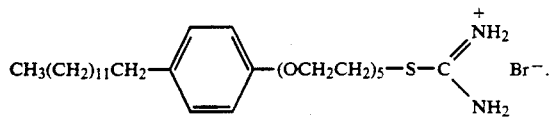

8. A composition as in claim 1 wherein the water soluble compound is of the formula:

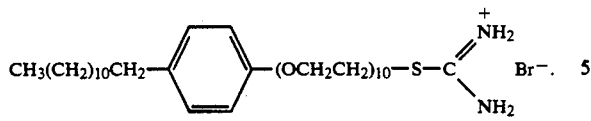

9. A composition as in claim 1 wherein the water soluble compound is of the formula:

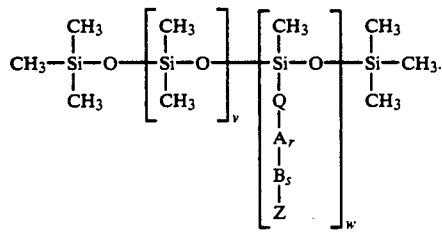

10. A composition as in claim 9 wherein the weight average molecular weight is about 4200.

11. A composition as in claim 9 wherein the weight average molecular weight is about 5200.

12. Aqueous compositions useful as hair conditioners for human hair containing an excipient which is acceptable in such hair conditioning compositions together with a mixture of water soluble compounds of the formula:

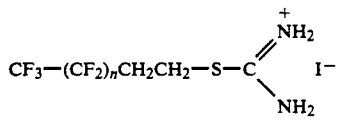

wherein n is 3 to 13.

13. A process for conditioning human hair which comprises treating the hair with an aqueous composition containing a water soluble compound of the formulas:

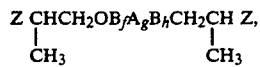

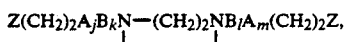

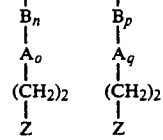

$R_2(CH_2)_xZ$ or

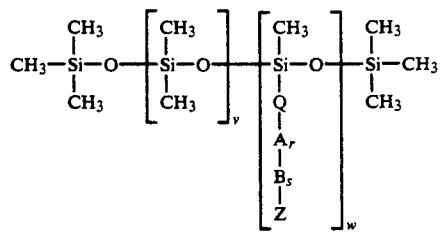

wherein
- $R_1$ is an alkyl or arylalkyl, the alkyl having about 12 to 24 carbons;
- $R_2$ is a perfluoroalkyl having about 4 to 16 carbons;
- A is an ethoxy group;
- B is a propoxy group;
- Z is an isothiuronium halide group;
- Q is an alkylene group having about 2 to 5 carbon atoms;
- a through s are integers designating the degree of ethoxylation and/or propoxylation or both, v is an integer of about 5 to 500, w is an integer of about 5 to 200 and x is an integer from about 0 to 4 in an amount which is effective when hair is treated by contact with the composition for from about 5 to about 30 minutes to improve the combability of the hair compared with hair which has not been so treated.

14. A process as in claim 13 wherein the water soluble compound is the formula:

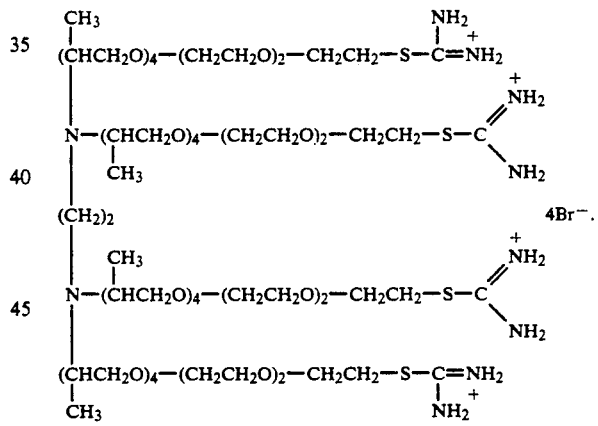

15. A process as in claim 13 wherein the water soluble compound is the formula:

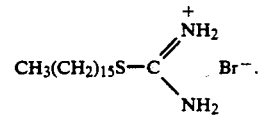

16. A process as in claim 13 wherein the water soluble compound is the formula:

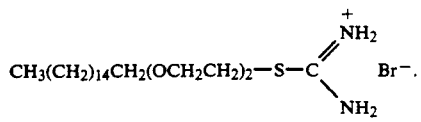

17. A process as in claim 13 wherein the water soluble compound is the formula:

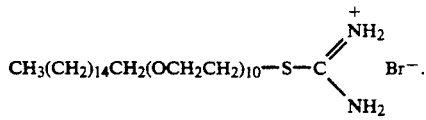

18. A process as in claim 13 wherein the water soluble compound is the formula:

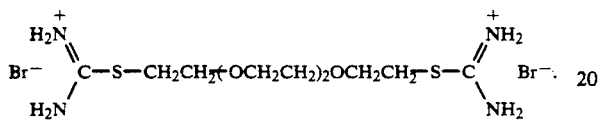

19. A process as in claim 13 wherein the water soluble compound is the formula:

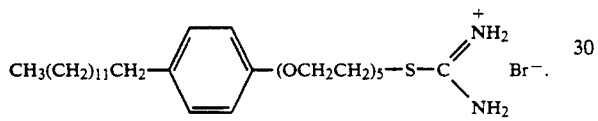

20. A process as in claim 13 wherein the water soluble compound is the formula:

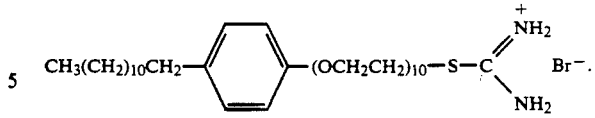

21. A process as in claim 13 wherein the water soluble compound is the formula:

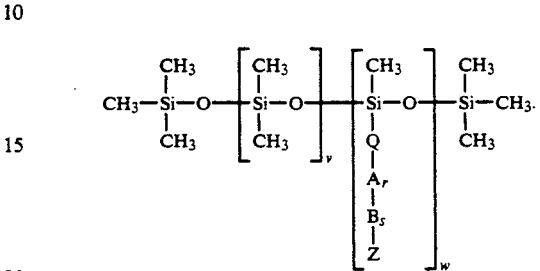

22. A process as in claim 21 wherein the weight average molecular weight of the compound is about 4200.

23. A process as in claim 21 wherein the weight average molecular weight of the compound is about 5200.

24. A process for conditioning human hair which comprises treating the hair with an aqueous mixture containing water soluble compounds of the formula

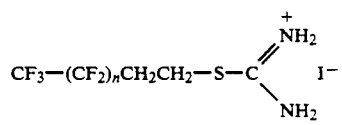

wherein n is 3 to 13.

* * * * *